(12) United States Patent
Gattrell

(10) Patent No.: US 8,907,144 B2
(45) Date of Patent: Dec. 9, 2014

(54) PROCESS FOR ADIABATIC PRODUCTION OF MONONITROTOLUENE

(75) Inventor: Michael Gattrell, Vancouver (CA)

(73) Assignee: NORAM International Limited, Dublin (IE)

( * ) Notice: Subject to any disclaimer, the term of this patent is extended or adjusted under 35 U.S.C. 154(b) by 237 days.

(21) Appl. No.: 13/427,688

(22) Filed: Mar. 22, 2012

(65) Prior Publication Data

US 2013/0253233 A1 Sep. 26, 2013

(51) Int. Cl.
C07C 205/00 (2006.01)
C07B 41/00 (2006.01)
C07C 27/26 (2006.01)

(52) U.S. Cl.
USPC ............ 568/939; 568/940; 568/950; 568/958

(58) Field of Classification Search
CPC .. C07C 201/08; C07C 205/06; C07C 201/16; C07C 205/12
USPC ................................. 568/939, 940, 950, 958
See application file for complete search history.

(56) References Cited

U.S. PATENT DOCUMENTS

| | | |
|---|---|---|
| 2,256,999 A | 9/1941 | Castner |
| 4,021,498 A | 5/1977 | Alexanderson et al. |
| 4,091,042 A | 5/1978 | Alexanderson et al. |
| 4,650,912 A | 3/1987 | Pohl et al. |
| 5,313,009 A | 5/1994 | Guenkel et al. |
| 5,648,565 A | 7/1997 | Konig et al. |
| 6,506,949 B2 | 1/2003 | Gillis et al. |
| 6,583,327 B2 | 6/2003 | Demuth et al. |
| 7,781,624 B2 | 8/2010 | Rausch et al. |
| 2003/0055300 A1 | 3/2003 | Chrisochoou et al. |

OTHER PUBLICATIONS

G. Booth, "Aromatic Nitro Compounds", Ullmann's Encyclopedia of Industrial Chemistry (Weinheim: Wiley-VCH, 2005).
M. Dugal, "Nitrobenzene and Nitrotoluenes", in Kirk-Othmer Encyclopedia of Chemical Technology, 5th ed, vol. 17 (New York: John Wiley & Sons, 2005).
A.A. Guenkel, "Nitrobenzene and Nitrotoluene", in J.J. McKetta & W.A.Cunningham, eds, Encyclopedia of Chemical Processing and Design (New York: Marcel Dekker, 1990).
H. Hermann et al, "Industrial Nitration of Toluene to Dinitrotoluene", in L.F. Albright et al, eds, Nitration: Recent Laboratory and Industrial Developments, ACS Symposium Series 623, Chapter 21 (Washington: American Chemical Society, 1996).
A.A. Guenkel et al, "Recent Advances in the Technology of Mononitrobenzene Manufacture" in L.F. Albright et al, eds, Nitration: Recent Laboratory and Industrial Developments, ACS Symposium Series 623, Chapter 20 (Washington: American Chemical Society, 1996).
R.H. Perry et al, eds, Perry's Chemical Engineers' Handbook, 7th ed (New York: McGraw-Hill, 1999) at 2-78 and 2-79.
C. Hanson et al, "Side Reactions During Aromatic Nitration" in L.F. Albright et al, eds, Industrial and Laboratory Nitrations, ACS Symposium Series 22, Chapter 8 (Washington: American Chemical Society, 1976).
H. Cerfontain et al, "The Solubility of Toluene and Benzene in Concentrated Aqueous Sulphuric Acid: Implications to the Kinetics of Aromatic Sulfonation" (1965) 84:5 Recueil des Travaux Chimiques des Pays-Bas 545.
J.L. Gustin, "Runaway Reaction Hazards in Processing Organic Nitro Compounds" (1998) 2 Organic Proc. Res. & Dev 27.
J.M. Zaldivar et al, "Aromatic Nitrations by Mixed Acid. Fast Liquid-Liquid Reaction Regime" (1996) 35 Chem. Eng. & Proc. 91.
J.T. Davies, "A Physical Interpretation of Drop Sizes in Homogenizers and Agitated Tanks, Including the Dispersion of Viscous Oils" (1987) 42:7 Chem. Eng. Sci. 1671.
C.M. Evans, "Practical Considerations in Concentration and Recovery of Nitration Spent Acids" in L.F. Albright et al, eds, Nitration: Recent Laboratory and Industrial Developments, ACS Symposium Series 623, Chapter 22 (Washington: American Chemical Society, 1996).

*Primary Examiner* — Jafar Parsa
(74) *Attorney, Agent, or Firm* — Oyen Wiggs Green Mutala LLP

(57) ABSTRACT

A process for continuous adiabatic nitration of toluene to mononitrotoluene (MNT). The process yields a product quality of MNT that is comparable to that obtained by isothermal production. The process uses excess toluene, with the reaction rate being controlled to maintain a residual of 0.003-0.102 wt % nitric acid in the spent acid and an orange to red color of the spent acid. Further process conditions include re-concentrated sulfuric acid at 83 to 99 degrees C. with a concentration of sulfuric acid from 66 to 70.5 wt %. This is mixed with nitric acid to generate a mixed acid with 1.0 to 3.8 wt % nitric acid and toluene is added at a rate of 1.1 to 1.71 moles toluene/mole nitric acid. The reactants are mixed in a reactor with an overall average mixing intensity of 5.8 to 19 W/kg of contained solution.

17 Claims, 3 Drawing Sheets

PROCESS FOR ADIABATIC PRODUCTION OF MONONITROTOLUENE

TECHNICAL FIELD

The invention pertains to an adiabatic process for the continuous production of mononitrotoluene (MNT) by nitration of toluene.

BACKGROUND OF THE INVENTION

The nitration of toluene can produce three MNT isomeric products. Most industrially-produced MNT is further nitrated to dinitrotoluene (DNT), which is used in the production of toluene diisocyanate (TDI), a component of polyurethane. However, some MNT production focuses on the pure MNT isomers for smaller specialty chemical markets with the major uses being the production of dyes, rubber chemicals, and agricultural chemicals.

The production of MNT, either as a product in itself or as an intermediate for DNT, is typically carried out using isothermal mixed acid nitration. The "mixed acid" or "nitrating acid" is a mixture of nitric and sulfuric acids with sufficiently strong acidity to generate the nitronium ion (equation 1), which is the key reactant for the nitration reaction (equation 2).

The toluene has a low solubility in the mixed acid and so forms a second phase when they are mixed together. Because of this low solubility of toluene in the mixed acid and the rapid rate of the nitration reaction, the reaction takes place in the acid phase within a thin diffusion layer. The reaction is also exothermic. Because of these two factors, industrial reaction vessels are well mixed both to generate a large interfacial area between the two phases for the reaction and to provide good heat transfer to the reactor cooling coils to keep the reaction isothermal and avoid thermal runaway. To avoid excessive by-product formation, the reactions are typically carried out at around 25-60 degrees C.

The overall result of equations 1 and 2 is the generation of MNT and water, with the sulfuric acid acting as a catalyst and not being consumed. The product from the reactor is typically decanted to produce an organic product phase and a "spent acid" phase. The spent acid phase contains the sulfuric acid catalyst, but also the water generated by the overall nitration reaction. Because of this, the acid must be re-concentrated before it can be re-used. This involves heating the spent acid, typically under some vacuum, to remove the excess water, and this represents a significant energy demand for this process, as shown in the isothermal nitration of FIG. 1.

Adiabatic nitration involves carrying out a carefully controlled amount of nitration without reactor cooling, resulting in a targeted amount of temperature rise of the organic and nitrating acid mixture. After product separation, the hot spent acid is re-concentrated by flashing under vacuum. In this way the reaction heat is used to drive the spent acid re-concentration, resulting in a significant energy savings. This approach is widely used in the production of mononitrobenzene (MNB) from benzene and it would be highly desirable to use adiabatic nitration for the production of MNT. However, to achieve the maximum energy savings, this acid recycling loop requires integration of the nitrator temperature rise with the acid re-concentration step. A further constraint is imposed by the economically available vacuum for the acid re-concentration, which then requires a sufficient temperature to achieve a given concentration of sulfuric acid. For the transition of MNB from isothermal to adiabatic production this resulted in increased nitrator operating temperatures, which would be expected to lead to higher by-product formation. However, the increased reaction rate at the higher temperatures allowed for shorter reaction times, and the ease of acid re-concentration made operating with less total reaction per pass practical, with the net result being good product quality and significant energy savings. However, toluene is more susceptible to oxidation side reactions than benzene, and also the product MNT is more easily oxidized than MNB, and so shifting to higher reaction temperatures as would be required for an adiabatic MNT process is more problematic due to the increased potential for by-products. The integration of the nitration reactor and the acid re-concentration also decreases the temperature of the acid re-concentration, which has the potential to cause problems with the build-up of impurities in the acid loop that might otherwise be decomposed or vaporized at a higher acid re-concentration temperature (see for example Demuth et al., U.S. Pat. No. 6,583,327).

There are three routes to by-products during the nitration of toluene to form MNT. The largest amount and range of by-products is formed by nitric acid-driven oxidation reactions of both the toluene and the MNT product. These reactions lead to a range of products including cresols (methylphenols) and benzoic acids as well as products from their further oxidation and nitration. The second class of by-products is generated by over nitration and predominately consists of dinitrotoluenes (DNTs). The potential third class of by-products is sulfonated compounds generated by reaction of aromatic compounds with strong sulfuric acid, though these tend to be significant only at higher sulfuric acid concentrations (more than about 75 wt % sulfuric acid).

Industrially, the oxidation by-products are removed by alkaline washing, generating a highly colored aqueous waste stream referred to as "red water." Oxidation by-products therefore represent a waste of chemicals as well as additional costs related to the disposal of the red water. In DNT production, it is reported that the isothermal toluene to MNT stage can generate on average about 0.72 wt % cresols. Thus any adiabatic process should not generate significantly more than this amount.

The key difference in requirements between MNT production for MNT itself versus MNT as an intermediate for DNT, involves the acceptable levels of DNT by-product. If the product MNT is to be further nitrated to DNT, then the presence of by-product DNT is obviously not of concern. However, if the target product is MNT, the DNT by-products must be removed. The DNT by-products remain in the product after the alkaline washing and are typically removed as part of the distillation of the product MNT into its isomer fractions. As well as representing a waste of chemicals, high levels of DNT are a processing concern for the distillation. This is because DNT is less thermally stable than the MNTs and so care must be taken in the operation of the distillation process, with the related dangers and operational issues becoming more severe with higher DNT levels in the MNT product.

Therefore, for an adiabatic MNT process to be successful it should not unduly increase the by-product levels versus the isothermal process. Within this patent application, targets for the sum of cresols and benzoic acids less than 1 wt % (<10,000 ppm) and for DNTs less than 0.5 wt % (<5,000 ppm) are considered as consistent with a viable adiabatic process for the production of MNT.

An adiabatic approach to the production of MNT has been described in Konig et al., U.S. Pat. No. 5,648,565. However, the tests described in Konig et al. are based on simple batch testing using a stirred beaker. It is known that operating adiabatically using conditions as specified in Konig et al. but including re-concentrating and re-using the sulfuric acid quickly results in a build-up of organic compounds in the recycled acid. See, for example Demuth et al., U.S. Pat. No. 6,583,327. This would pose a problem for long-term industrial operation of the process described in Konig et al.

SUMMARY OF THE INVENTION

The invention provides a continuous adiabatic process for the production of MNT by the nitration of toluene. Toluene and a mixed acid comprising nitric acid, sulfuric acid and water are fed into a nitration reactor. The molar ratio of the toluene to the nitric acid is greater than 1. The two-phase mixture of toluene and mixed acid is passed through the reactor to react the toluene with the mixed acid, producing MNT and a spent acid phase.

The values of the reaction parameters are selected such that the nitric acid is not fully consumed, so the spent acid phase contains some unreacted nitric acid, and such that the produced MNT comprises less than 0.5 wt % DNT and less than 1 wt % cresols plus benzoic acids. An organic phase comprising the MNT is separated from the spent acid phase. The spent acid phase is concentrated to produce a concentrated sulfuric acid, and the concentrated sulfuric acid is recycled back to the reactor.

The reaction parameters that are controlled such that the reaction does not fully consume the nitric acid comprise the nitric acid concentration in the mixed acid, the sulfuric acid concentration in the mixed acid, the reactor inlet temperature, the concentration and temperature of the recycled sulfuric acid, the molar ratio of the toluene to the nitric acid, the average mixing intensity in the reactor, and the residence time in the reactor. The residual nitric acid in the spent acid is at least 0.003 wt %.

Further aspects of the invention and features of specific embodiments are described below.

DETAILED DESCRIPTION OF EMBODIMENTS OF THE INVENTION

Figure 1:
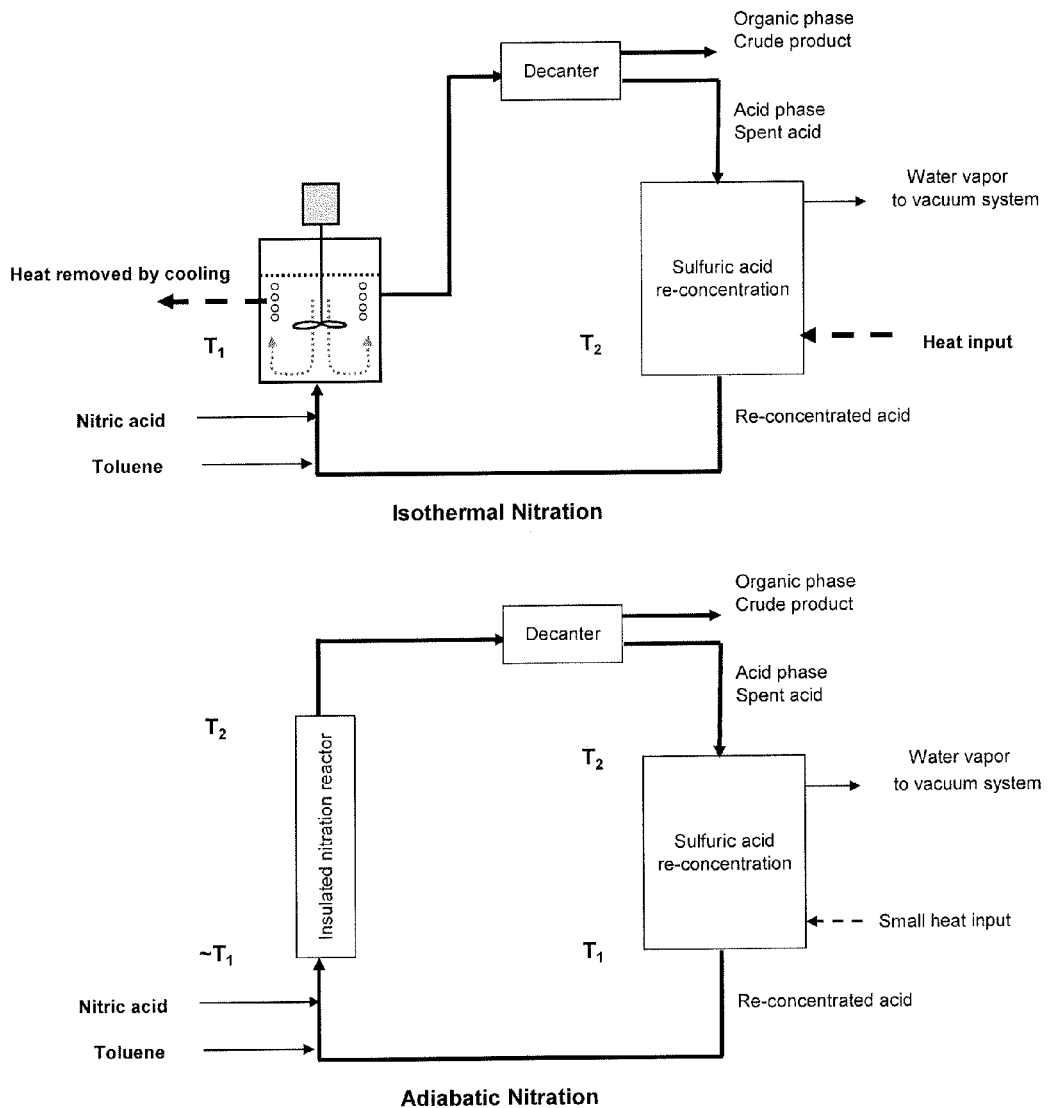
FIG. 1 shows two flowcharts depicting isothermal and adiabatic nitration processes for making MNT.

To investigate a continuous, adiabatic process for producing MNT, tests were carried out using a small-scale system including a complete acid recirculation loop allowing operation over multiple nitration-acid re-concentration cycles. From these tests a particular range of conditions that allow for adiabatic nitration of toluene to MNT with minimal by-products (i.e. that meet the by-product targets) and allow for stable operation with repeated recycling and re-use of the sulfuric acid have been identified.

To allow long-term continuous operation of an adiabatic MNT process, the reactor feed mixture should use a stoichiometric excess of toluene but with the reaction conditions chosen to achieve incomplete conversion within the nitration reactor and so to provide a spent acid with a small residual nitric acid concentration, just sufficient to give the spent acid an orange to red color. Adjusting the nitration reaction to meet this target for the spent acid properties involves adjusting the reaction rate. Because nitration occurs at the interface between the organic and acid phases, the reaction rate is described by:

$$\text{rate}_{MNT} = a x_{Tol} C_{Tol}^* \sqrt{k_{MNT} C_{HNO3} D_{Tol}} \quad [3]$$

where:
  a = the interfacial area
  $x_{Tol}$ = is the mole fraction of toluene in the organic phase
  $C_{Tol}^*$ = the solubility of pure toluene in the acid phase
  $k_{MNT}$ = is the chemical rate constant for toluene nitration
  $C_{HNO3}$ = the bulk concentration of nitric acid
  $D_{Tol}$ = the diffusion coefficient of toluene in the acid phase The solubility of toluene in the acid phase ($C_{Tol}^*$) increases with higher temperature and with a higher concentration of sulfuric acid. The reaction rate ($k_{MNT}$) also increases with higher temperature and with a higher concentration of sulfuric acid (the catalyst); and the diffusion coefficient of toluene in the acid phase ($D_{Tol}$) increases with higher temperature and decreases with a higher concentration of sulfuric acid.

For a simple reactor like a continuously stirred tank reactor (CSTR) at steady state with a low volume fraction of dispersed phase (less than about 10%), the interfacial area is related to:

$$a = \frac{6\varphi}{C_1} \left(\frac{\rho}{\sigma}\right)^{3/5} \varepsilon^{2/5} \quad [4]$$

where:
  $\Phi$ = the organic phase volume fraction
  $\rho$ = is the acid phase density
  $\sigma$ = is the interfacial tension between the organic and acid phases
  $C_1$ = is a constant for the mixing device
  $\varepsilon$ = turbulent energy dissipation (W/kg or m$^2$/s$^3$)

and where, at steady state, the average turbulent energy dissipation equals the inputted mixing power per kg of solution. For a pipe type reactor the inputted mixing power is related to the reactor pressure drop times the flow rate.

And so factors such as temperature, sulfuric acid strength, nitric acid concentration, toluene volume fraction and mixing power, will contribute to the nitrator reaction rate and can be adjusted to achieve the target residual nitric acid in the spent acid, for a given residence time in the reactor and reactor geometry.

In addition to the method of operation allowing for stable continuous operation, a second requirement is to determine operating conditions that can achieve the required product quality. Specifically, the sum of cresols and benzoic acids is to be less than 1 wt % (<10,000 ppm) and DNT is to be less than 0.5 wt % (<5,000 ppm).

The reaction to produce DNT is a slow reaction occurring between dissolved MNT and nitric acid throughout the acid phase, and so given by:

$$\text{rate}_{DNT} = k_{DNT} x_{MNT} C_{MNT}^* C_{HNO3} \quad [5]$$

where:
  $x_{MNT}$ = is the mole fraction of MNT in the organic phase
  $C_{MNT}^*$ = the solubility of pure MNT in the acid phase
  $k_{DNT}$ = is the chemical rate constant for MNT nitration
  $C_{HNO3}$ = the bulk concentration of nitric acid The fraction of by-product DNT produced per product MNT would be given by combining equations 3 and 5:

$$\frac{\text{rate}_{DNT}}{\text{rate}_{MNT}} = \frac{k_{DNT} x_{MNT} C^*_{MNT} C_{HNO3}}{a x_{Tol} C^*_{Tol} \sqrt{k_{MNT} C_{HNO3} D_{Tol}}} \quad [6]$$

$$= \left( \frac{C^*_{MNT} k_{DNT}}{C^*_{Tol} \sqrt{k_{MNT} D_{Tol}}} \right) \left( \frac{x_{MNT}}{x_{Tol}} \right) \frac{\sqrt{C_{HNO3}}}{a}$$

The values in the first bracket in equation 6 are constants that are affected by temperature and sulfuric acid concentration. While the relationships are complex, increased temperature and increased sulfuric acid concentration both generally increase the DNT produced per product MNT. This can be seen in the equivalent performances obtained using higher acid strength and lower temperature (Example 3 below) or higher temperature and lower acid strength (Example 4). Other factors have a clearer effect, such as increasing interfacial area will decrease the DNT produced per product MNT. Interfacial area can be increased by increasing the toluene volume fraction and/or the mixing power (see equation 4). Also, because the amount of toluene added to the nitration reactor is proportional to the nitric acid feed (typically reported as a mole ratio), the square root nitric acid concentration will be divided by the proportional toluene volume fraction included in the interfacial area term. The net effect will then be a decrease in DNT produced per product MNT with increased nitric acid feed (i.e. increased reaction per pass through the nitration reactor as specified by the nitric acid concentration in the mixed acid entering the nitration reactor).

Thus, in searching for reaction conditions to lower the amount of DNT by-product, one should consider:

For a given toluene/nitric acid stoichiometry, higher nitric acid concentrations in the mixed acid decrease the DNT/MNT production ratio.

Higher sulfuric acid concentrations increase the DNT/MNT production ratio.

Higher temperature increases the DNT/MNT production ratio.

A higher organic/acid phase ratio decreases the DNT/MNT production ratio.

The production of oxidation by-products such as cresols and benzoic acids is more complex and less well characterized than DNT formation. However, an experimental investigation by Hanson et al. (C. Hanson, T Kaghazchi and M. W. T. Pratt, "Side reactions during aromatic nitration", in L. F. Albright and C. Hanson (Eds.) "Industrial and Laboratory Nitrations", ACS Symp. Series 22, Ch 8, 132-155, 1976) on oxidation by-product formation for toluene nitration under isothermal conditions found the following general trends:

Nitrous acid ($HNO_2$) was generated in proportion to by-product formation (and was used as a marker for by-product formation throughout their work).

Higher nitric acid concentrations increased the $HNO_2$/MNT production ratio.

Higher sulfuric acid concentrations decreased the $HNO_2$/MNT production ratio.

Higher temperature increased the $HNO_2$/MNT production ratio.

A higher organic/acid phase ratio increased the $HNO_2$/MNT production ratio.

And so, other than temperature, the suggested approaches to lower oxidation by-products are opposite to those to lower DNT. A further complication for a practical adiabatic process is that the temperature and concentration of the re-concentrated sulfuric acid are linked by the available vacuum. Thus, for example, lowering the temperature of the re-concentrated acid also results in a lower strength of the re-concentrated acid. This raises the question of whether there actually exists a window of operating conditions that will allow an adiabatic MNT process to meet the constraints of sum of cresols and benzoic acids less than 1 wt % (<10,000 ppm) and DNTs less than 0.5 wt % (<5,000 ppm), while also maintaining the target residual nitric acid in the spent acid to allow long-term operation. To determine if such a window existed, a series of tests were carried out with varying process conditions. The tests which resulted in successful process conditions are listed in Table 1 below.

Figure 3:
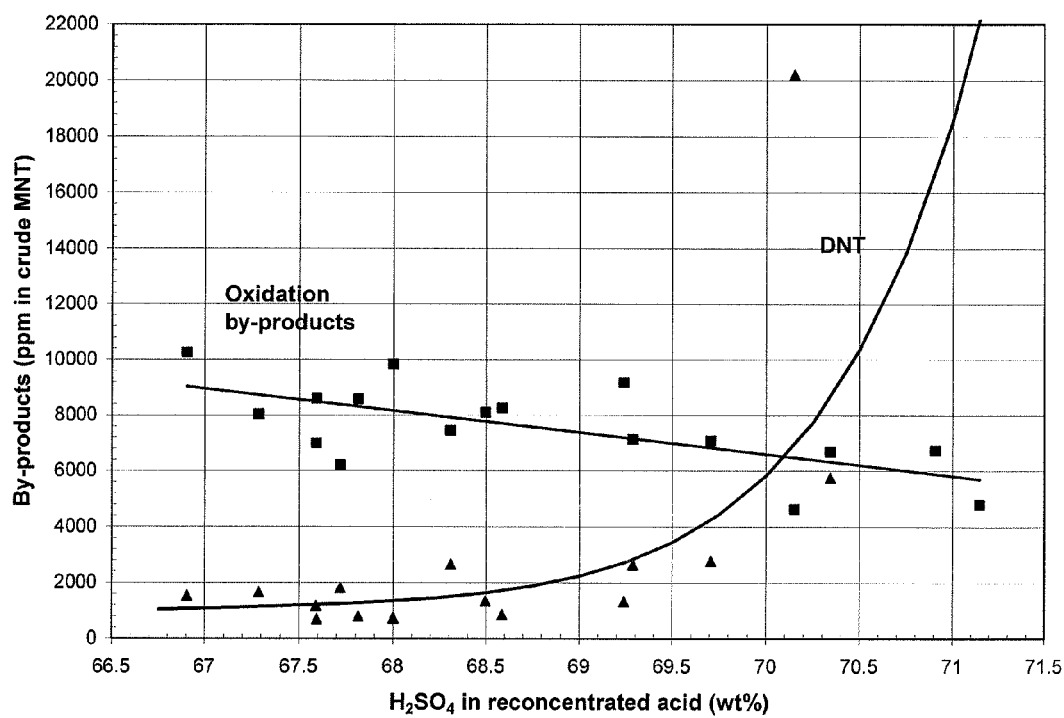
FIG. 3 is a graph of sulfuric acid concentration of the re-concentrated acid versus the concentration of oxidation by-products from the adiabatic production of MNT.

FIG. 3 plots the data taken from all the examples herein as a function of the re-concentrated acid strength. While other factors also play a role, one can see the general trends discussed above with higher sulfuric acid strength increasing DNT and decreasing the amount of oxidation by-products. This result is actually far more complex than it appears in FIG. 3. For a given water vapor pressure in the sulfuric acid re-concentrator, there is a relationship between the sulfuric acid strength and the temperature. Thus, generally, the higher sulfuric acid strengths in FIG. 3 are related to higher sulfuric acid re-concentrator temperatures and so also to higher reactor inlet temperatures (some cooling of the re-concentrated acid occurs because the feed nitric acid and toluene were at room temperature). A second issue is that for a given sulfuric acid strength and acid re-concentrator temperature, the nitric acid and toluene feeds were adjusted to achieve red spent acid. Therefore, variations in the nitric acid and toluene feeds are not entirely independent of the sulfuric acid strength, adding additional complexity to any fundamental interpretation of FIG. 3. However, from a practical viewpoint, FIG. 3 shows a window of conditions which have been found to successfully produce adiabatic MNT with repeated acid recycling and while achieving a product with less than 1 wt % (<10,000 ppm) of cresols plus benzoic acids and less than 0.5 wt % (<5,000 ppm) DNT.

From Table 1 and FIG. 3, this window of successful process conditions for the laboratory test system can be described as:
Re-concentrated acid strength: 66.5-70 wt %
Re-concentrated acid temperature: 85-97 degrees C.
Nitric acid in the mixed acid: 1.4-3.8 wt %
Toluene/nitric acid stoichiometric ratio: 1.14-1.71
Mixing intensity 5.8-8.8 W/kg
Residual nitric acid in the spent acid: 0.003-about 0.100 wt %
Sulfuric acid strength in the mixed acid: 63.4-66.6 wt %
Nitrator inlet temperature: 82-93 degrees C.

However, because of equipment limitations, the reactor inlet pressure used in the small lab system was limited to 100 psi (6.8 bar), thus limiting the nitration reactor pressure drop and so the mixing intensity. Industrial nitrators however can be operated at higher pressure drops with an unfouled value of 13.5 bar (Rausch et al., U.S. Pat. No. 7,781,624), a tubular reactor with 4 to 12 mixing plates with a preferred pressure drop of 0.5 to 1.2 bar per plate (14.4 bar) (Chrisochoou et el., US 2003/0055300), and a tubular reactor with 7 to 25 mixing plates with a maximum pressure drop of 0.7 bar per plate (17.5 bar) (Gillis et al., U.S. Pat. No. 6,506,949). Thus at least 2.5 times the pressure drop and so 2.5 times the mixing power intensity (about 19 W/kg) would be expected to be achievable in an industrial nitration reactor. Referring to equation 4, this would be expected to result in about a 1.45 times increase in interfacial area. Even higher pressure drops would of course lead to further increases in interfacial area, though because of the ⅔ power on the turbulent energy dissipation term in equation 4, ever higher pressure drops offer limiting returns.

Considering a 1.45 times increase in interfacial area, this would be predicted to increase the reaction rate as indicated by equation 3 by 45% allowing, for example, a lower temperature, lower acid strength and/or a lower residence time to be used to achieve a target conversion and so a target residual nitric acid. Such an increase in interfacial area would also be expected to lower the DNT produced per product MNT as indicated by equation 6. For example, using a 1.45 times increased interfacial area, then the process conditions for the lab scale reactor generating 7,200 ppm DNT in MNT might be expected to meet the 5,000 ppm DNT in MNT target if the mixing intensity in a full sized industrial nitration reactor was 2.5 times higher. Referring to FIG. 3, this would allow about 0.5 wt % higher sulfuric acid strength, which would also be associated with about 1.5 degrees C. higher acid re-concentration temperature. Alternatively, the increased mixing could allow 45% less excess toluene to be used to achieve the same interfacial area, or for a fixed toluene to nitric acid stoichiometry, less reactant loading per pass (as indicated here by the nitric acid strength in the mixed acid). For the oxidation by-products the direct impact of mixing is more complex. However, as mentioned above, the higher reaction rate provided by a higher interfacial area could allow the use of a lower temperature which will help decrease the production of oxidation by-products allowing a lower minimum acid strength (and associated re-concentration temperature). Thus the range of successful process conditions given above based on the lab test system might be considered to be preferred ranges, with wider ranges possible with a higher mixing intensity, full sized industrial nitration reactor, namely:

Re-concentrated acid strength: 66-70.5 wt %
Re-concentrated acid temperature: 83-99 degrees C.
Nitric acid in the mixed acid: 1.0-3.8 wt %
Toluene/nitric acid stoichiometric ratio: 1.1-1.71
Mixing intensity 5.8-19 W/kg, alternatively 8-18 W/kg
Residual nitric acid in the spent acid: 0.003-about 0.100 wt %, alternatively 0.003-0.050 wt %
Sulfuric acid strength in the mixed acid: 62.9-67.1 wt %
Nitrator inlet temperature: 80-85 degrees C.

Thus, through continuous testing using a complete acid recycling loop, the process of adiabatic nitration of toluene to MNT has been investigated. This testing has found problems that could be a barrier to the continuous adiabatic production of MNT, but also identified a solution to these problems. Further, within the context of the discovered solution that allows long-term continuous operation, a range of process conditions has been identified that can yield a product quality of MNT that is reasonably comparable to the quality obtained by isothermal MNT production. This allows the practice of adiabatic nitration of MNT with a resultant energy savings by using the reaction heat for the recycling of the spent sulfuric acid.

EXAMPLES

Figure 2:
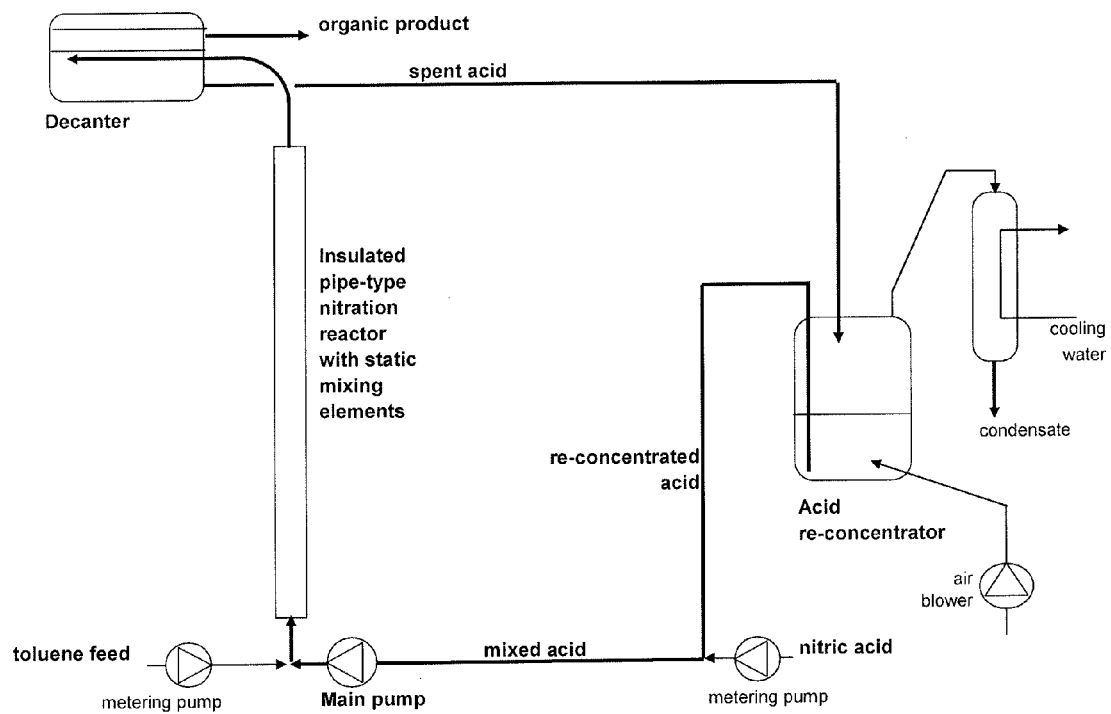
FIG. 2 is a schematic drawing of a system for carrying out the adiabatic nitration process of the invention.

Testing was carried out using a small-scale nitration loop of the type shown in FIG. 2. A main pump re-circulated the sulfuric acid and two metering pumps added controlled amounts of nitric acid and toluene. Following the pumps was a small insulated pipe reactor containing static mixers acting as the adiabatic nitration reactor. The combinations of reactor volume and flowrates used in the tests were such that the residence time in the reactor was in the range of 55 to 75 seconds. After the reactor there was a decanting vessel where the organic product and spent acid phases were allowed to separate. From the decanting vessel the spent acid went to a re-concentrator, thus closing the acid recirculation loop. The acid re-concentrator used air stripping to remove water vapor to a target partial pressure within the re-concentrator, providing similar performance to the vacuum-based systems used for full scale nitration facilities. Using this system, tests could be carried out with different sulfuric acid strengths, different starting temperatures (in the acid re-concentrator) and different feed rates of nitric acid and toluene. At typical acid re-circulation rates used in these tests, the sulfuric acid volume was turned over in about 12-15 minutes and so 1 hour of testing involved 4-5 re-uses of the sulfuric acid. The system could produce about 1 kg of product per hour.

The spent acid and re-concentrated acid were analyzed for nitric and nitrous acids by ion chromatography and for sulfuric acid either by titration (followed by correction for any nitric acid and nitrous acid) or using an Anton Paar analyzer. The decanted organic product was analyzed by GC for toluene, 2-MNT, 3-MNT, 4-MNT, 2,4-DNT, 2,6 DNT, 4-methyl-2-nitrophenol, 2-methyl-3-nitrophenol and 4-methyl-3-nitrophenol. It was also analyzed by HPLC for: 5-methyl-2-nitrophenol, 3-methyl-4-nitrophenol, 2-methyl-5-nitrophenol, 4-methyl-4,6-dinitrophenol, 2-methyl-4,6-dinitrophenol, 2-nitrobenzoic acid, 3-nitrobenzoic acid, 4-nitrobenzoic acid, 4-hydroxy-3-nitrobenzoic acid, 2-hydroxy-5-nitrobenzoic acid, 2,4-dinitrobenzoic acid and 3,5-dinitrobenzoic acid. Other compounds are formed that are not captured by this analysis; however, this analysis provides a good overview of the effect of different reaction conditions on the product quality. Also, to allow the comparison of results with different residual toluene concentrations, the reported by-product concentrations are given as ug per g of MNT (ppm in the MNT) as opposed to ppm in the total decanted organic product. Finally, a small amount of additional clean MNT (<5% additional) was recovered with the condensed water from the acid re-concentration, which is not included in these calculations.

The reported average nitrator mixing intensities provided in the examples were obtained by nitrator pressure drop× flowrate/(nitrator volume×solution density) giving a value in W/kg or $m^2/s^3$.

Comparative Example 1

The re-concentrated sulfuric acid was 70.3 wt % and at 99.9 degrees C. 60 wt % nitric acid was metered in to achieve a mixed acid containing 3.03 wt % nitric acid. Toluene was added at 1.25 moles of toluene/moles nitric acid. The nitrator inlet temperature was 93.1 degrees C. and the resulting decanter temperature was 122.0 degrees C. The average nitrator mixing intensity was 5.9 W/kg. The decanted product contained 5,759 ppm DNT, 6,175 ppm cresols and 515 ppm benzoic acids. The spent acid contained 0.000 wt % nitric acid and 0.000 wt % nitrous acid. The decanted product also contained 12.8 wt % toluene, consistent with 100% conversion of the nitric acid. The spent acid started off a golden yellow color, by 75 minutes or about 6 turnovers of the sulfuric acid the color was reddish-orange, the color then turned dark red by 120 minutes (about 10 turnovers), and finally became black at more than 200 minutes (about 15 turnovers). The black acid is foamy, which caused problems for the decanter with rising bubbles carrying acid-containing foam out with the upper organic phase. Eventually tarry deposits began to appear within the acid loop. Thus, this represents a reaction condition which is not suitable for long term operation.

Comparative Example 2

The re-concentrated sulfuric acid was 69.2 wt % and at 97.2 degrees C. 60 wt % nitric acid was metered in to achieve a mixed acid containing 2.52 wt % nitric acid. Toluene was added at 1.31 moles of toluene/moles nitric acid. The nitrator inlet temperature was 93.2 degrees C. and the resulting decanter temperature was 115.4 degrees C. The average nitrator mixing intensity was 8.1 W/kg. The spent acid composition was 67.7 wt % sulfuric acid, 0.000 wt % nitric acid and 0.000 wt % nitrous acid. The decanted product contained 1,323 ppm DNT, 8,458 ppm cresols and 707 ppm benzoic acid. The decanted product also contained 17.0 wt % toluene, consistent with 100% conversion of the nitric acid. After 65 minutes of operation (about 5 turnovers) the spent acid was dark red in color and the sample at 117 minutes (about 9 turnovers) was black.

Comparative Examples 1 and 2 were carried out under conditions described in Konig et al., U.S. Pat. No. 5,648,565. These examples used a stoichiometric excess of toluene and the reaction was allowed to proceed to completion with the feed nitric acid being fully consumed by the decanter outlet. This approach is also consistent with typical adiabatic MNB production.

The product quality was good for Comparative Example 2 and had high DNT for Comparative Example 1. However, in these examples, when the spent acid was re-concentrated and re-used, after 2-3 hours of operation or about 9-15 acid re-use cycles, the acid turned black in color. The black colored acid was foamy, which could cause problems for the decanter and possibly the acid re-concentrator, and eventually tarry deposits began to appear within the acid loop. Black acid can also occur in isothermal production of MNT and can cause difficulties for the acid purification. While different solutions have been proposed, the simplest approach is to avoid contacting the acid phase with excess toluene. This phenomenon represents a clear difference between benzene and toluene nitration.

Comparative Example 3

The re-concentrated sulfuric acid was 70.9 wt % and at 92.6 degrees C. 60 wt % nitric acid was metered in to achieve a mixed acid containing 2.59 wt % nitric acid. Toluene was added sub-stoichiometrically at 0.93 moles of toluene/moles nitric acid (i.e. excess nitric acid). The nitrator inlet temperature was 89.8 degrees C. and the resulting decanter temperature was 109.8 degrees C. The average nitrator mixing intensity was 7.5 W/kg. The spent acid composition was 69.2 wt % sulfuric acid, 0.225 wt % nitric acid and 0.204 wt % nitrous acid. The decanted product contained 43,127 ppm DNT, 3,006 ppm cresols and 3,733 ppm benzoic acid. The decanted product also contained 8.8 wt % toluene, corresponding to about 87% conversion of the starting toluene. The resulting spent acid was yellow in color and the system operated under these conditions for 300 minutes or about 25 turnovers of the sulfuric acid.

In Comparative Example 3 the nitration reactor was fed excess nitric acid. This approach is consistent with typical isothermal MNT production. In this case the spent acid was yellow and remained that color over 5 hours or about 25 acid re-use cycles with no sign of black acid. However, it was found that under these conditions unacceptably high levels of DNT were produced. One contributing factor is thought to be the fact that the spent acid will contain a significant amount of dissolved MNT along with the excess nitric acid, allowing additional nitration to occur throughout the acid re-concentration and re-cycling. Having this excess nitric acid present in the acid loop may also lead to some oxidation of the dissolved MNT as suggested by the significantly higher levels of benzoic acids than the other examples.

Comparative Example 4

The re-concentrated sulfuric acid was 71.1 wt % and at 92.0 degrees C. 60 wt % nitric acid was metered in to achieve a mixed acid containing 2.57 wt % nitric acid. Toluene was added at 1.07 moles of toluene/moles nitric acid. The nitrator inlet temperature was 89.0 degrees C. and the resulting decanter temperature was 110.9 degrees C. The average nitrator mixing intensity was 8.0 W/kg. The spent acid composition was 69.6 wt % sulfuric acid, 0.087 wt % nitric acid and 0.308 wt % nitrous acid. The decanted product contained 22,890 ppm DNT, 3,419 ppm cresols and 1,380 ppm benzoic acid. The decanted product also contained 12.8 wt % toluene, corresponding to about 88% of the targeted toluene conversion. The resulting spent acid was orange in color and the system operated under these conditions for 250 minutes or about 20 turnovers of the sulfuric acid.

Comparative Example 5

The re-concentrated sulfuric acid was 70.2 wt % and at 99.0 degrees C. 60 wt % nitric acid was metered in to achieve a mixed acid containing 2.57 wt % nitric acid. Toluene was added at 1.10 moles of toluene/moles nitric acid. The nitrator inlet temperature was 95.7 degrees C. and the resulting decanter temperature was 117.0 degrees C. The average nitrator mixing intensity was 8.0 W/kg. The spent acid composition was 68.4 wt % sulfuric acid, 0.110 wt % nitric acid and 0.624 wt % nitrous acid. The decanted product contained 20,201 ppm DNT, 3,634 ppm cresols and 1,007 ppm benzoic acid. The decanted product also contained 8.2 wt % toluene corresponding to about 97% of the targeted toluene conversion. The resulting spent acid was orange-red in color and the system operated under these conditions for 400 minutes or about 30 turnovers of the sulfuric acid.

Comparative Examples 4 and 5 show the use of excess toluene, but in these examples the reaction conditions were chosen to achieve only close to complete reaction, while leaving a small residue of nitric acid in the spent acid (targeting less than 0.1 wt % residual nitric acid). In these examples the spent acid was orange to red and remained this color over the course of the test. The DNT concentration in Comparative Examples 4 and 5, while lower than Comparative Example 3 was still excessive, while the benzoic acid concentration was much lower. While the DNT concentrations in these examples were too high, the examples do serve to illustrate how fairly equivalent performances can be obtained, at least over a small range, using higher acid strength and lower temperature (Comparative Example 4) or higher temperature and lower acid strength (Comparative Example 5).

The spent acid color was also found to correlate with the oxidation state of the sample. The oxidation state of a few samples was measured at room temperature using an oxidation-reduction potential (ORP) probe. The yellow acid samples were found to give readings that started around 800-850 mV vs Ag/AgCl and climbed to around 1000 mV over a few minutes. Orange to red samples gave readings around 700-800 mV. And dark red-brown to black samples gave readings from about 550-650 mV.

Examples 6-17

Nitrations were carried out in accordance with the procedure described above using the nitration loop shown in FIG. 2.

The values of the reaction parameters and the results are set out in Table 1. These nitrations were all satisfactory, with acceptable levels of by-products and stable operation with repeated recycling of the sulfuric acid.

TABLE 1

Testing results

| | Reconcentrated acid | | | Mixed acid | | Toluene | | Reactor Mixing | | | Spent acid | | Crude product | |
|---|---|---|---|---|---|---|---|---|---|---|---|---|---|---|
| | | | water | | | Toluene/ HNO$_3$ | | | | | | residual | DNT | oxidation by-products |
| Example | Temp. C | H$_2$SO$_4$ wt % | vapor mbar | HNO$_3$ wt % | H$_2$SO$_4$ wt % | stoichi-ometry | Vol. % (at T$_{in}$) | power W/kg | T$_{in}$ C | T$_{out}$ C | H$_2$SO$_4$ wt % | HNO$_3$ wt % | ppm in MNT | ppm in MNT |
| 6 | 97.0 | 69.3 | 84 | 3.12 | 65.7 | 1.23 | 9.7 | 8.6 | 92.7 | 120.6 | 67.3 | 0.013 | 2,642 | 7,131 |
| 7 | 96.0 | 68.6 | 88 | 2.53 | 65.7 | 1.31 | 8.4 | 8.1 | 92.3 | 114.5 | 66.7 | 0.004 | 861 | 8,272 |
| 8 | 94.0 | 68.0 | 86 | 2.83 | 64.8 | 1.28 | 9.1 | 8.4 | 89.5 | 114.0 | 66.3 | 0.003 | 737 | 9,841 |
| 9 | 93.1 | 67.6 | 86 | 2.83 | 64.4 | 1.28 | 9.0 | 8.5 | 88.7 | 113.6 | 65.7 | 0.010 | 687 | 8,600 |
| 10 | 93.5 | 67.8 | 86 | 2.83 | 64.6 | 1.28 | 9.1 | 8.8 | 89.5 | 114.2 | 65.8 | 0.010 | 813 | 8,582 |
| 11 | 92.5 | 67.3 | 87 | 2.66 | 64.3 | 1.32 | 8.7 | 7.1 | 87.6 | 111.2 | 65.7 | 0.006 | 1,669 | 8,033 |
| 12 | 92.5 | 67.6 | 84 | 2.65 | 64.6 | 1.34 | 8.9 | 5.8 | 87.8 | 110.9 | 65.9 | 0.007 | 1,168 | 6,987 |
| 13 | 93.0 | 66.9 | 93 | 1.44 | 65.3 | 1.72 | 6.4 | 6.6 | 91.0 | 101.8 | 66.3 | 0.005 | 1,543 | 10,247 |
| 14 | 92.2 | 67.7 | 82 | 3.80 | 63.4 | 1.14 | 10.6 | 7.4 | 86.7 | 120.6 | 65.2 | 0.041 | 1,810 | 6,217 |
| 15 | 85.0 | 68.5 | 54 | 2.69 | 65.4 | 1.31 | 8.8 | 7.4 | 81.8 | 106.3 | 66.8 | 0.010 | 1,344 | 8,106 |
| 16 | 89.0 | 69.7 | 56 | 2.65 | 66.6 | 1.28 | 8.6 | 6.8 | 85.9 | 109.5 | 68.0 | 0.012 | 2,776 | 7,090 |
| 17 | 96.5 | 68.3 | 92 | 2.73 | 65.3 | 1.24 | 8.5 | 7.2 | 91.8 | 114.8 | 67.0 | 0.102 | 2,660 | 7,447 |

As will be apparent to those skilled in the art in the light of the foregoing disclosure, many alterations and modifications are possible in the practice of this invention without departing from the scope thereof. Accordingly, the scope of the invention is to be construed in accordance with the following claims.

The invention claimed is:

1. A continuous adiabatic process for the production of mononitrotoluene, comprising:
    (a) feeding into a reactor toluene and a mixed acid, the mixed acid comprising nitric acid, sulfuric acid and water, the molar ratio of the toluene to the nitric acid being greater than 1, the toluene and the mixed acid comprising a two-phase mixture;
    (b) passing the two-phase mixture through the reactor to react the toluene with the mixed acid, producing mononitrotoluene and a spent acid phase;
    (c) selecting the values of the reaction parameters such that the nitric acid is not fully consumed and the spent acid phase contains at least 0.003 wt % nitric acid and such that the produced mononitrotoluene comprises less than 0.5 wt % dinitrotoluene and less than 1 wt % of cresols plus benzoic acids;
    (d) separating an organic phase comprising the mononitrotoluene from the spent acid phase;
    (e) concentrating the spent acid phase to produce a concentrated sulfuric acid; and
    (f) recycling the concentrated sulfuric acid for use in step (a).

2. A process according to claim 1, wherein the reaction parameters comprise the nitric acid concentration in the mixed acid, the sulfuric acid concentration in the mixed acid, the reactor inlet temperature, the concentration of the recycled sulfuric acid, the temperature of the recycled sulfuric acid, the molar ratio of the toluene to the nitric acid, the average mixing intensity in the reactor, and the residence time in the reactor.

3. A process according to claim 1, wherein the mixed acid comprises 1.0-3.8 wt % nitric acid, the concentration of the recycled sulfuric acid is in the range of 66-70.5 wt %, the temperature of the recycled sulfuric acid is in the range of 83-99 degrees C., the molar ratio of the toluene to the nitric acid is in the range of 1.1-1.71, and the average mixing intensity is in the range of 5.8-19 W/kg.

4. A process according to claim 3, wherein the concentration of sulfuric acid in the mixed acid in the range of 62.9-67.1 wt %.

5. A process according to claim 3, wherein the concentration of sulfuric acid in the mixed acid in the range of 63.4-66.6 wt %.

6. A process according to claim 3, wherein the reactor inlet temperature in the range of 80-95 degrees C.

7. A process according to claim 3, wherein the reactor inlet temperature in the range of 82-93 degrees C.

8. A process according to claim 1, wherein the spent acid phase produced in step (b) is mildly oxidizing and orange to red in color.

9. A process according to claim 1, wherein the concentration of the unreacted nitric acid in the spent acid phase is in the range of 0.003-0.102 wt %.

10. A process according to claim 1, wherein the concentration of the unreacted nitric acid in the spent acid phase is in the range of 0.003-0.05 wt %.

11. A process according to claim 3, wherein step (d) is done at a temperature up to 130 degrees C.

12. A process according to claim 3, wherein the residence time is in the range of 55-75 seconds.

13. A process according to claim 3, wherein the average mixing intensity is in the range of 8-18 W/kg.

14. A process according to claim 3, wherein the temperature of the recycled sulfuric acid is in the range of 85-97 degrees C.

15. A process according to claim 1, wherein the reactor comprises a plug flow reactor having static mixing elements.

16. A process according to claim 1, wherein the reactor comprises two or more continuous stirred tank reactors in series.

17. A process according to claim 1, wherein the reactor comprises a combination of one or more plug flow reactors having static mixing elements and one or a series of continuous stirred tank reactors.

* * * * *